United States Patent [19]

Lee

[11] 4,268,674
[45] May 19, 1981

[54] PREPARATION OF SUBSTITUTED OXATRIAZOLES

[75] Inventor: George A. Lee, Wayland, Mass.

[73] Assignee: The Dow Chemical Company, Midland, Mich.

[21] Appl. No.: 57,640

[22] Filed: Jul. 16, 1979

Related U.S. Application Data

[60] Continuation-in-part of Ser. No. 851,016, Nov. 14, 1977, abandoned, which is a division of Ser. No. 789,179, Apr. 20, 1977.

[51] Int. Cl.³ .......................................... C07D 273/00
[52] U.S. Cl. .................................................. 548/125
[58] Field of Search ...................... 260/307 R, 307 H; 548/125, 128

[56] References Cited

U.S. PATENT DOCUMENTS

| | | | |
|---|---|---|---|
| 2,713,581 | 7/1955 | Pannone | 260/308 D |
| 3,435,048 | 3/1969 | Iwai et al. | 260/307 H |
| 3,711,495 | 1/1973 | Kulsa et al. | 260/307 D |
| 3,956,343 | 5/1976 | Crawley et al. | 260/307 H |
| 4,057,549 | 11/1977 | Adelstein et al. | 260/293.54 |
| 4,139,363 | 2/1979 | Ziman | 548/125 |

FOREIGN PATENT DOCUMENTS 1227144 4/1971 United Kingdom .

OTHER PUBLICATIONS

Kirk–Othmer, Encyclopedia of Chemical Technology, 2nd Ed., vol. 5, pp. 7–13.
Weber et al., "Phase Trans. Cat. in Org. Syn.", Springer Verlag, (NY), 1977.
Grundmann, Synthesis II, pp. 344–359, (1970).
Fusco et al., "Chim. Ind.", (Milan) 1975.
Starks et al., JACS, vol. 93, pp. 195–199.
Huisgen et al., "Tetrahedron Letters," (1966), pp. 405–409.

Primary Examiner—Anton H. Sutto
Attorney, Agent, or Firm—Charles J. Enright

[57] ABSTRACT

The title compounds are prepared by a convenient, one-step liquid process comprising contacting with agitation, a liquid mixture comprising both:
  (a) an oxime, and
  (b) an azo compound
with an oxidizing amount of an aqueous alkali(ne earth) metal hypohalite. For example, stirring a liquid mixture of dimethylazodicarboxylate and benzaldoxime with aqueous sodium hypochlorite produces a good yield of dimethyl-4-phenyl-2,3-dihydro-1,2,3,5-oxatriazole-2,3-dicarboxylate.

12 Claims, No Drawings

PREPARATION OF SUBSTITUTED OXATRIAZOLES

CROSS-REFERENCE TO RELATED APPLICATION

This is a continuation-in-part of copending application Ser. No. 851,016, filed Nov. 14, 1977, now abandoned, which is a division of copending application Ser. No. 789,179, filed Apr. 20, 1977.

BACKGROUND OF THE INVENTION

1. Field of the Invention

This invention relates to a process for preparing substituted oxatriazoles from the reaction of an oxime with an azo compound. This invention also relates to the production of certain addition compounds from the reaction of an oxatriazole with an azo compound.

2. Description of the Prior Art

Grundman, "Synthesis of Heterocyclic Compounds with the Aid of Nitrile Oxides," *Synthesis, II*, 344 (1970), surveys known methods of preparing substituted 5-membered heterocycles, e.g., oxatriazoles, via a nitrile oxide ($-C\equiv N^{\oplus}-O^{\ominus}$) intermediate. These are two-step methods comprising first oxidizing an oxime to a halogenated species, e.g., hydroximic acid chlorides, and second dehydrohalogenating the halogenated species in the presence of an unsaturated compound, e.g., an azo compound. The dehydrohalogenating of the halogenated species generates a nitrile oxide which then condenses with the available unsaturated compound in a 1,3-dipolar cycloaddition. While many variations on each step are known, a convenient one-step process has yet to be reported. Grundman, supra, is here incorporated by reference.

SUMMARY OF THE INVENTION

According to this invention, an oxatriazole of the formula

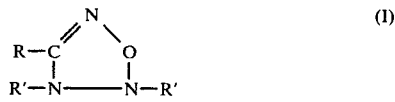

is conveniently prepared by a one-step, liquid process comprising contacting in a liquid reaction medium and with agitation an oxime of the formula

with an azo compound of the formula

with an oxidizing amount of an aqueous alkali(ne earth) metal hypohalite where:

R is $C_1$–$C_8$ alkyl, $C_6$–$C_{20}$ aromatic hydrocarbon or an inertly-substituted alkyl or aromatic hydrocarbon radical, and R' is —COOR and each R' can be the same or different.

As here used, the term "inertly-substituted" means that the substituents on the aliphatic or aromatic radicals (R or R') are essentially nonreactive with the process reagents or products. Typical substituents include halogen, ether oxygen, carbonyl, ester, alkyl, cycloalkyl, aryl, etc.

Although the oxatriazoles are produced in good yields, these compounds are relatively unstable and are frequently recovered as an open-chain compound which is the product of a reaction between the oxatriazole and a second mole of the oxime (via the nitrile oxide intermediate). The oxatriazoles are useful intermediates in the manufacture of dyes.

DETAILED DESCRIPTION OF THE INVENTION

Both the reactants and products of this invention are known compounds. The oximes are of formula II and preferably R is a $C_1$–$C_8$ alkyl or a $C_6$–$C_{12}$ aromatic hydrocarbon radical. Illustrative oximes include ethyl-, propyl-, butyl-, hexyl-, octyl-, cyclopentyl-, cycloheptyl-, ω-chloropropyl-, isobutyl- and neopentylaldehyde oxime, benzaldoxime, 2,4,6-trimethylbenzyl oxime, 4-nitrobenzyl oxime, 2,6-dichlorobenzyl oxime and the like.

The azo compounds of this invention are esters of azodicarboxylic acid of formula III. R is preferably a $C_1$–$C_8$ alkyl or $C_6$–$C_{12}$ aromatic hydrocarbon radical. Although each R' can be the same or different, typically they are the same. Illustrative azo compounds include dimethyl-, diethyl-, dipropyl-, diphenyl-, dibenzyl-, methylethyl-, ethylphenyl-, cyclopentylpropyl-, cycloheptyloctyl-, ω-chloropropylethyl-, isobutylbenzyl- and ω-chlorobutylhexylazodicarboxylate and the like. The aliphatic azodicarboxylates are preferred to the aromatic azodicarboxylates and the $C_1$–$C_4$ alkyl azodicarboxylates are the preferred aliphatic azodicarboxylates.

The compounds of formulae II and III are believed to combine in a concerted, 4-centered 1,3-dipolar cycloaddition to form an oxatriazole compound. This cycloaddition involves the generation of a nitrile oxide intermediate from the oxime and is stereospecific, i.e., the configurational character of the azo compound is maintained.

Aqueous alkali or alkaline earth metal hypohalites are necessary for the practice of this invention. Any suitable hypohalite can be used but for reasons of convenience, the alkali metal hypohalites, especially sodium or potassium hypochlorite and hypobromite, are preferred. Although the alkali(ne earth) metal hypohalites can be used either per se or generated in situ, the former is preferred over the latter because the latter can result in the oxidation of some of the azo compound. This in turn results in less azo compound available for the 1,3-dipolar cycloaddition with the oxime and thus lowers the yield of the reaction.

Sufficient hypohalite to oxidize the oxime to the nitrile betaine is employed. Generally, the hypohalite and the oxime are present at a minimum hypohalite:oxime mole equivalent ratio of about 1:1 and preferably of about 1.2:1. Practical considerations, such as product recovery and economics, are the only limitations upon the maximum hypohalite:oxime mole equivalent ratio but for reasons of convenience, a maximum mole equivalent ratio of about 5:1 is preferred and a ratio of about 3:1 more preferred.

Stoichiometric amounts of the oxime and azo compound are typically employed. However, a minimum azo:oxime mole equivalent ratio of about 0.1:1 can be used but for reasons of yield considerations, a minimum ratio of about 0.7:1 is preferred. Here too, only practical considerations limit the maximum azo:oxime mole equivalent ratio that can be used but for reasons of convenience a maximum ratio of about 10:1 is preferred with a maximum of about 3:1 more preferred.

The liquid reaction medium of this invention can be either homogeneous (monophasic) or heterogeneous (bi- or multiphasic). If the former is desired, a solvent capable of dissolving all reagents is necessary, such as tetrahydrofuran, since the reagents are generally immiscible with each other, i.e., the oxime and azo compound generally form an organic phase and the hypohalite is generally in an aqueous phase. If the latter is desired, the invention can be practiced either neat or in the presence of at least one water-immiscible organic solvent. The invention is usually practiced neat if all the reagents are liquid or if the nonliquid reagents are soluble in the liquid reagents. For example, if a solid oxime is used, an azo compound can serve as a solvent if it dissolves the oxime. (Under such conditions, the azo compound is used generally in excess of stoichiometric amounts, e.g., more than 1 equivalent). Neat reaction (process) conditions are preferred because they are generally more efficient than solvent conditions as regards cost, convenience and yield. Of course, where nonliquid reagents are not soluble in the other reagents, the invention is practiced in the presence of a suitable solvent. Representative solvents include methylene chloride, chloroform, benzene, o-dichlorobenzene, ethylacetate and the like.

Heterogeneous liquid reaction mediums are usually preferred. Heterogeneous conditions lend themselves readily to reaction monitoring and product recovery. Moreover, substrates having additional functional groups that are reactive with aqueous hypohalite are generally unsuitable for homogeneous conditions because of undesirable side reactions. For example, substrates having an $\alpha,\beta$-unsaturated carbonyl can undergo Michael addition across the double bond and oximes can be oxidized to acids. These side reactions are negligible if the invention is practiced under heterogeneous conditions.

The liquid reaction mediums of this invention are also agitated. Neither the amount nor form of agitation is critical and thus it can be varied to choice.

Where this invention is practiced under heterogeneous conditions, it can be further promoted by the use of a phase transfer catalyst, here defined to include both onium salts and tertiary amines. Any onium salt or tertiary amine that will promote the formation of a nitrile betaine is suitable. Preferred tertiary amines are of the formula $R_1R_2R_3N$ where $R_1$–$R_3$ are individually hydrocarbyl radicals, e.g., alkyl, aryl, aralkyl, cycloalkyl, etc., of 1 to about 20 carbon atoms each. Tertiary amines where $R_1$–$R_3$ are individually alkyl radicals of 1 to 4 carbon atoms each are especially preferred. Illustrative tertiary amines include triethyl-, tripropyl-, tributyl-, ethyldipropyl-, methyldibutyl-, methylethylpropyl-, benzyldiethyl-, phenethylpropyl-, methylphenyldiethyl-, diphenylmethylamine, and the like.

The onium salts here used are described by Starks and Napier in Br. Pat. No. 1,227,144 and by Starks in *J. Amer. Chem. Soc.*, 93, p. 195 (1971). Suitable onium salts have a minimum solubility of at least about 1 weight percent in both the organic and the aqueous phase at 25° C. For reasons of availability, the ammonium and phosphonium salts are preferred and tri-n-butylmethyl-, triphenylmethyl-, benzyltriethyl-, and tetra-n-butylammonium and phosphonium chlorides, bromides and bisulfates are most preferred.

As a further illustration of the type of onium salts here used, suitable onium salts are represented by the formula $R_4R_5R_6R_7Q^+A^-$ wherein $Q^+$ is a quaternized nitrogen or phosphorus atom, $R_4$–$R_7$ are hydrocarbyl groups and $R_4$ can join with $R_5$, $R_5$ with $R_6$, etc. to form a 5- or 6-membered heterocyclic compound having at least one quaternized nitrogen or phosphorus atom in the ring and may also contain one nonadjacent atom of nitrogen or oxygen within the ring. Typically, $R_4$–$R_7$ are hydrocarbyl radicals of from 1 to about 16 carbon atoms each with a combined minimum total of about 10 carbon atoms. Preferred ammonium salts have from about 10 to about 30 carbon atoms.

The neutralizing anion portion of the salt, i.e., $A^-$ in the above formula, may be varied to convenience. Chloride and bisulfate are the preferred anions but other representative anions include fluoride, bromide, iodide, tosylate, acetate, etc. The following compounds serve as a nonlimiting illustration: tetraalkylammonium salts, such as tetra-n-butyl-, tri-n-butylmethyl-, tetrahexyl-, trioctylmethyl-, hexadecyltriethyl-, and tridecylmethylammonium chlorides, bromides, iodides, bisulfates, tosylates, etc.; alkylarylammonium salts, such as tetrabenzyl-, benzyltrimethyl-, benzyltriethyl-, benzyltributyl-, and phenethyltrimethylammonium chlorides, bromides, iodides, etc.; arylammonium salts, such as triphenylmethylammonium fluoride, chloride or bromide, N,N,N-trimethyl-N-phenylammonium chloride, N,N,N-triethyl-N-phenylammonium bromide, N,N-diethyl-N,N-diphenylammonium bisulfate, trimethylnaphthylammonium chloride, p-methylphenyltrimethylammonium chloride or tosylate, etc; 5- and 6-membered heterocyclic compounds containing at least 1 quaternary nitrogen atom in the ring, such as N,N-dibutylmorpholinium chloride, etc., and the corresponding phosphonium salts.

A catalytic amount of the phase transfer catalyst is employed if such a catalyst is used in the practice of this invention. The concentration will vary with the particular reagents employed but best results are generally achieved when the maximum catalyst concentration is about 15 mole percent and preferably about 10 mole percent, with a minimum phase transfer catalyst concentration of about 1 mole percent and preferably about 5 mole percent (based on the moles of oxime).

Product yield is little effected by the order in which the reagents are contacted. In other words, whether the oxime is added to the azo compound/hypohalite or whether the hypohalite is added to the oxime/azo compound little effects the ultimate product yield. However, it has been found to be advantageous to gradually contact the oxime with a mixture of aqueous hypohalite and azo compound, generally via a drop-addition of the former to the latter. Such addition allows ready consumption of the nitrile oxide by the available azo compound and minimizes the competitive dimerization of the nitrile oxide.

While temperature and pressure can be varied, temperatures in excess of about 50° C. can result in product and reagent destruction while temperatures less than about −25° C. are without advantage. Since the reaction produces a moderate exotherm, the contacting (reaction) is preferably conducted via drop-addition and at subambient temperatures (less than about 25° C.), and most preferably at temperatures between about −20° C. and 15° C., inclusive. Autogenous pressure is also preferred.

The oxatriazoles produced by this invention are relatively unstable compounds and are frequently difficult to isolate. Typically, these compounds undergo ring cleavage isomerization to an open-chain compound which is susceptible to attack by a second mole of nitrile oxide (oxime) to produce an addition product of the formula $$R-C\begin{array}{c}N-O-R'\\ \diagdown\\ N=N\\ \diagdown\\ C-R\\ R'-O-N\end{array}\quad (IV)$$

Due to the azo group, these addition compounds are generally colored, typically yellow.

The following examples are illustrative embodiments of this invention. Unless indicated to the contrary, all parts and percentages are by weight.

SPECIFIC EMBODIMENTS

EXAMPLE 1

A 125 ml Erlenmeyer flask was charged with dimethylazodicarboxylate (1.46 g, 0.01 mole), triethylamine (0.1 g, 0.00099 mole), methylene chloride (15 ml) and 11 percent aqueous sodium hypochlorite (20 ml, 2.46 g NaOCl, 0.036 mole). The reaction contents were magnetically stirred in an ice methanol bath ($-15°$ C.) while a solution of benzaldoxime (1.21 g, 0.01 mole) in methylene chloride (10 ml) was added dropwise over 1 hour. After the completion of the oxime addition, the reactants were stirred for an additional 12 hours. The methylene chloride phase was then separated and washed twice with water and dried over anhydrous magnesium sulfate. Removal of the solvent afforded a reddish-orange paste which was dissolved in absolute ethanol. Cooling this solution produced yellow crystals (melting point 181° C.-183° C., Dec) which were subsequently identified by proton magnetic resonance, infrared, elemental and molecular weight analysis to be the rearranged azodicarbonate (V) (0.48 g, 25 percent of theoretical yield).

$$CH_3OC-O-N\begin{array}{c}\\ \diagdown\\ \\ N=N\\ \phi-C\diagup\\ \\ N-OCOCH_3\\ \|\\ O\end{array}C-\phi\quad (V)$$

$\phi \equiv$ phenyl

The azodicarbonate is an addition product of this invention, i.e., a product formed by the reaction of the oxatriazole product with a second mole of the benzaldoxime. The formation of this addition product is further described by Huisgen et al., *Tetrahedron Letters*, 405–409 (1966).

Example 2

The procedure of Example 1 was repeated except after the methylene chloride phase was separated and washed twice with water and dried over anhydrous magnesium sulfate, the solvent was removed from the reddish-orange paste, condensed and then subjected to high pressure liquid chromatography. This analysis confirmed the presence of the azocarboxylate of formula VI (0.27 g, 10 percent of theory).

$$\phi-C\begin{array}{c}O\\ \|\\ N-OCOCH_3\\ \diagdown\\ N=N-CO_2CH_3\end{array}\quad (VI)$$

The azocarboxylate had a melting point of 93° C.–94° C. and a proton magnetic resonance spectrum essentially identical to that reported by Huisgen, supra.

The azocarboxylate is the rearranged oxatriazole produced by this reaction, i.e., thermally rearranged dimethyl-4-phenyl-2,3-dihydro-1,2,3,5-oxatriazole-2,3-dicarboxylate (VII).

$$\phi-C\begin{array}{c}N\\ \diagup\quad\diagdown\\ \quad\quad O\\ |\quad\quad|\\ H_3CO_2C-N-\!\!-\!\!-N-CO_2CH_3\end{array}\quad (VII)$$

The preceding examples are for illustrative purposes only and are not to be construed as a limitation upon the invention as described in the appended claims.

What is claimed is:

1. A process for preparing an oxatriazole of the formula $$R-C\begin{array}{c}N\\ \diagup\quad\diagdown\\ \quad\quad O\\ |\quad\quad|\\ R'-N-\!\!-\!\!-N-R'\end{array}\quad (I)$$

the process comprising the step of contacting in a liquid reaction medium and with agitation an oxime of the formula $$R-\overset{H}{\underset{|}{C}}=N-OH\quad (II)$$

with an azo compound of the formula $$R'-N=N-R'\quad (III)$$

and an oxidizing amount of an aqueous alkali or alkaline earth metal hypohalite, where:

R is $C_1$-$C_8$ saturated aliphatic, $C_6$-$C_{20}$ aromatic hydrocarbon or an inertly-substituted aliphatic or aromatic hydrocarbon radical, and R' is —COOR and each R' can be the same or different.

2. The process of claim 1 wherein the hypohalite and oxime are present at a hypohalite:oxime mole equivalents ratio between about 1:1 and about 5:1, inclusive.

3. The process of claim 1 wherein the hypohalite and the oxime are present at a hypohalite:oxime mole equivalents ratio between about 1.2:1 and about 3:1, inclusive.

4. The process of claim 2 wherein the azo compound and the oxime are present at an azo compound:oxime mole equivalents ratio between about 0.1:1 and about 10:1, inclusive.

5. The process of claim 3 wherein the azo compound and oxime are present at an azo compound:oxime mole equivalents ratio between about 0.7:1 and about 5:1, inclusive.

6. The process of claim 4 wherein the contacting is conducted at a temperature between about $-25°$ C. and about $50°$ C.

7. The process of claim 6 wherein R is $C_1$-$C_8$ alkyl or phenyl.

8. The process of claim 7 wherein the oxime, azo compound and aqueous hypohalite form a biphasic mixture.

9. The process of claim 8 wherein the contacting is conducted in the presence of a catalytic amount of at least one phase transfer catalyst.

10. The process of claim 9 wherein the catalyst is an onium salt of the formula $R_4R_5R_6R_7Q^+A^-$ wherein $Q^+$ is quaternized nitrogen or phosphorus atom, $A^-$ is a neutralizing anion, and $R_4$-$R_7$ are hydrocarbyl groups of from 1 to about 16 carbon atoms each with a combined minimum total of about 10 carbon atoms.

11. The process of claim 9 wherein the catalyst is triethylamine.

12. The process of claim 11 wherein the alkali metal hypohalite is sodium hypochlorite.

* * * * *